(12) United States Patent
Kersten et al.

(10) Patent No.: US 6,228,607 B1
(45) Date of Patent: May 8, 2001

(54) BIOREACTOR

(75) Inventors: Jean Kersten, Villers-Saint-Amand (BE); Augustinus Bader, Lehrte-Immensen (DE)

(73) Assignee: Organogenesis Inc., Canton, MA (US)

( * ) Notice: Subject to any disclaimer, the term of this patent is extended or adjusted under 35 U.S.C. 154(b) by 0 days.

(21) Appl. No.: 08/930,534

(22) PCT Filed: Apr. 22, 1996

(86) PCT No.: PCT/BE96/00045

§ 371 Date: Feb. 25, 1998

§ 102(e) Date: Feb. 25, 1998

(87) PCT Pub. No.: WO96/34087

PCT Pub. Date: Oct. 31, 1996

(30) Foreign Application Priority Data

Apr. 28, 1995 (BE) .................................................. 95000391

(51) Int. Cl.[7] ...................................................... C12P 1/00
(52) U.S. Cl. .................... 435/41; 435/297.1; 435/297.2; 435/297.4; 435/297.5; 435/325; 435/370; 435/398; 435/284.1
(58) Field of Search .............................. 435/297.1, 297.2, 435/297.4, 297.5, 41, 325, 370, 398, 284.1

(56) References Cited

U.S. PATENT DOCUMENTS

| | | | |
|---|---|---|---|
| 3,948,732 | 4/1976 | Haddad et al. | 195/127 |
| 5,290,700 | 3/1994 | Binot et al. | 435/284 |
| 5,516,691 | 5/1996 | Gerlach | 435/297.1 |
| 5,658,797 | * 8/1997 | Bader | 435/284.1 |

FOREIGN PATENT DOCUMENTS

| | | | | |
|---|---|---|---|---|
| 0113328 | 7/1984 | (EP) | | C12M/3/02 |
| 0363262 | 4/1990 | (EP) | | C12M/3/00 |
| 0419234 | 3/1991 | (EP) | | C12M/3/00 |
| 8501062 | 3/1985 | (WO) | | C12M/1/12 |
| 8900188 | 1/1989 | (WO) | | C12M/3/00 |
| 9013639 | 11/1990 | (WO) | | C12N/5/00 |
| 9318133 | 9/1993 | (WO) | | C12M/3/06 |

* cited by examiner

*Primary Examiner*—David A. Redding
(74) *Attorney, Agent, or Firm*—Hale and Dorr LLP

(57) ABSTRACT

The invention relates to a bioreactor for a cell treatment of a medium. Said bioreactor comprises an element defining a chamber in which cells for treating the medium are located, a liquid permeable membrane separating the said chamber from a first channel in which flows the medium to be treated, and a gas permeable membrane separating the said chamber from a second channel in which flows a gas containing oxygen.

34 Claims, 9 Drawing Sheets

BIOREACTOR

The Prior Art

Bioreactors for adherent cells are currently built of bundles of hollow fibers, with cells inside or outside the fibers or with a mass culture system inside or outside the fibers. The cells can be encapsulated in a polymer matrix, like collagen, alginate, etc.

All the known bioreactors suffer from the fact that adherent cells, and in particular hepatocytes, require confluence as a single layer to achieve an in-vivo equivalent metabolic function.

Problems of these known bioreactors are: geometry difficult to define accurately; and mass-transfer limitations.

Furthermore in all the known systems or bioreactors, the medium is first oxygenated and thereafter said oxygenated medium is treated by the cells.

The bioreactor of the invention aims to solve these problems. Furthermore, the bioreactor of the invention is suitable for treating media by cells without or with collagen overlay.

BRIEF DESCRIPTION OF THE INVENTION

The present invention relates to a bioreactor for a cell treatment of a medium. Said bioreactor comprises an element defining a chamber in which cells for treating the medium are located, a liquid permeable membrane separating the said chamber from a first channel in which flows the medium to be treated and a gas permeable membrane separating the said chamber from a second channel in which flows a gas containing oxygen.

Advantageously, the liquid permeable membrane has pores or openings with a diameter greater than 3 $\mu$m.

According to an embodiment, the bioreactor comprises two adjacent liquid permeable membranes, a first having pores or openings with a diameter greater than 3 $\mu$m, while the second has pores or openings with a diameter less than to 3 $\mu$m, preferably less than 0.5 $\mu$m.

This embodiment is particularly suitable when the cells used for the treatment are embedded in a collagen matrix or are covered with a collagen layer.

For example, the liquid permeable membrane can have hydrophobic characteristics or a combination of hydrophobic and hydrophylic characteristics.

According to a preferred embodiment, the bioreactor comprises a chamber containing cells, said chamber communicating with the channel in which flows the medium to be treated through a liquid permeable membrane and with the channel in which flows a gas containing oxygen through a gas permeable membrane, the chamber being provided with an outlet so as to remove medium issuing through the liquid permeable membrane from the channel in which flows the liquid medium to be treated. This outlet is very suitable for removing biliary compounds from the chamber, so as to maintain a better working of the cells in the chamber.

Advantageously, the chamber comprises at least two layers of cells, the layers being preferably separated from one another. A co-culture is thus possible in the chamber of the bioreactor. For example, Kupfer cell and hepatocyte cells can be used in the same chamber.

For example a first layer of cells contains a majority of Kupfer cells (for example, the layer adjacent to the channel for the flow of medium to be treated) or cells suitable to fix toxins, while the second layer contains a majority of hepatocyte cells.

According to a further embodiment, the chamber comprises an inlet and an outlet so that a flow of cell medium is possible.

According to another embodiment, the bioreactor comprises a plurality of stacked units consisting each of a frame provided with two layers so as to define therebetween a channel for the flow of a liquid medium or of a gas, one of said layers being a liquid permeable membrane or a gas permeable membrane. Preferably a cavity or passage is defined by or between the edges of the frame, one face of said cavity or passage being one of said layers, preferably a liquid permeable membrane.

According to another embodiment, the bioreactor comprises stacked units consisting each of a frame provided with a bottom layer so as to define a cavity for containing the cells for the treatment. Possibly pipes or fibres extend within the cavity and have liquid or gas permeable characteristics.

The invention relates also:
to units for a bioreactor according to the invention;
to a bioreactor system comprising a bioreactor, said bioreactor having an inlet for introducing medium to be treated to a liquid channel, an outlet for the medium flowing out of said liquid channel, an inlet for gas to flow into the bioreactor, an outlet for the gas flowing out of the bioreactor, and an outlet for collecting liquid flowing out of the chamber, the system being further provided with a means of filtering the liquid flowing out the chamber;
to processes using a bioreactor of the invention, and,
to a liver support (artificial liver or device for facilitating the function of a failing liver.

Major advantages of these embodiments for a bioreactor according to the invention includes:
the geometry of the bioreactor is accurately defined and allows better control of mass transfer;
the cells when used for treating a medium are oxygenated;
easy and simple construction;
possibly to use collagen as well as other matrix support;
possibility to treat biliary products and to evacuate biliary products from the chamber.

DESCRIPTION OF EMBODIMENTS ACCORDING TO THE INVENTION

Figure 1:
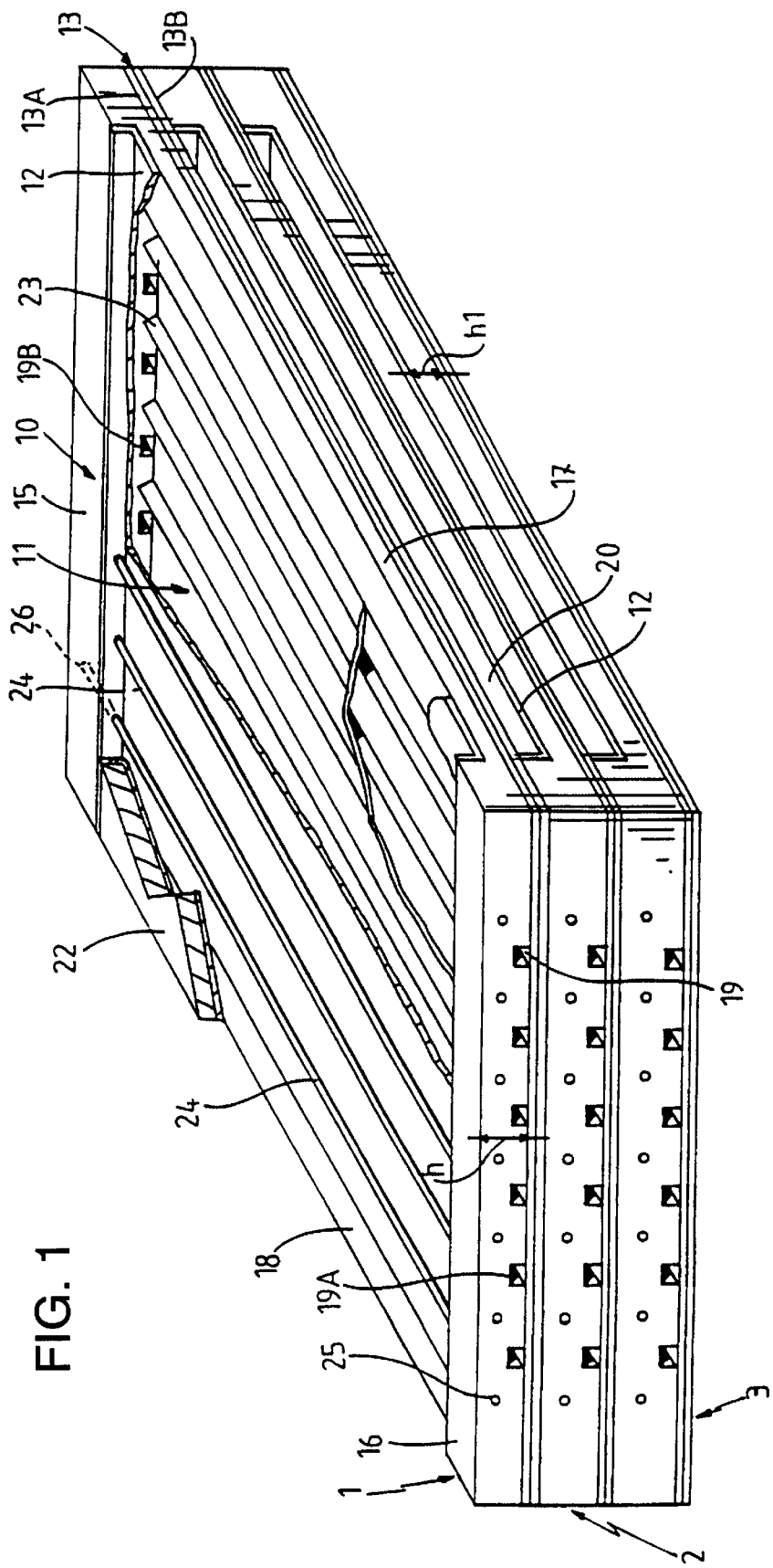
FIG. 1 is a partial perspective view with cross-sections of a bioreactor according to the invention.

The bioreactor of FIG. 1 for a cell treatment of a medium comprises a plurality of treatment units 1,2,3, ... which are stacked together.

Each unit consists of a frame 10 which is provided on both sides with a liquid permeable film 12,13, for example a film having a porosity of less than 3 microns, preferably less than 1 micron (for example 0.45 μm). A chamber 11 is so defined between the two porous films of the frame.

The frame consists of four rods 15,16,17,18, two opposite rods 15,16 having a height or thickness h greater than the thickness h1 of the two other rods 17,18, the latter each linking one end of the rod 15 to one end of the rod 16.

The frame has advantageously a substantially rectangular form. The rods or edges 15,16 are provided with engraved channels 19, while the rods 17,18 are plain.

The bottom porous film 13 extends in a plane, in which the first faces of the rods or edges (15,16,17,18) are located. The upper porous film 12 covers and is attached to the faces of the rods or edges 17,18 opposite to said first faces, so as to form between rods 15,16 a cavity or channel 20 that is located above the face of the film 12 opposite to the face of film 12 directed towards the frame 10.

The bottom of said cavity 20 is thus formed by the liquid permeable film 12.

The unit 1 is thus adapted to form with the adjacent unit 2 a chamber or volume 20 suitable to receive a medium or a matrix containing cells. For example, the cells can be entrapped into a collagen matrix 22 or between two layers of collagen. It is obvious that other material can be suitable for attaching cells. However, collagen is often preferred. The chamber contains advantageously two cell layers separated from one another by a collagen layer.

The medium to be treated enters through channels 19A (extending through edge 16) into the chamber 11. Due to the porous films 12,13 the medium is treated by the cells contained in the matrix 22. The treated medium flows out of the chamber 11 through channels 19B (extending through edge 15).

The chamber 11 is provided between the inlet channels 19A and the outlet channels 19B, with means 23 for directing the flow of medium in the chamber 11. Such means are for example protuberances borne by the bottom film 13. Other means are possible.

Within the open space or cavity 20 and between the edges 15 and 16 extend gas permeable fibers 24. Gas containing oxygen enters in the fibers through openings or holes 25 and flows out of said fibers through openings or holes 26 of the edge 15.

These fibers extend in the matrix 22 containing the cells so as to oxygenate the cells during the treatment.

Preferably, two adjacent membranes 13A,13B are used for forming the porous films 12,13. The membranes 13A directed towards the chamber 11 have pores with a diameter of about 0.45 μm, while the membranes 13B directed towards the cavity 20 have pores with a diameter of about 3 μm.

Figure 2:
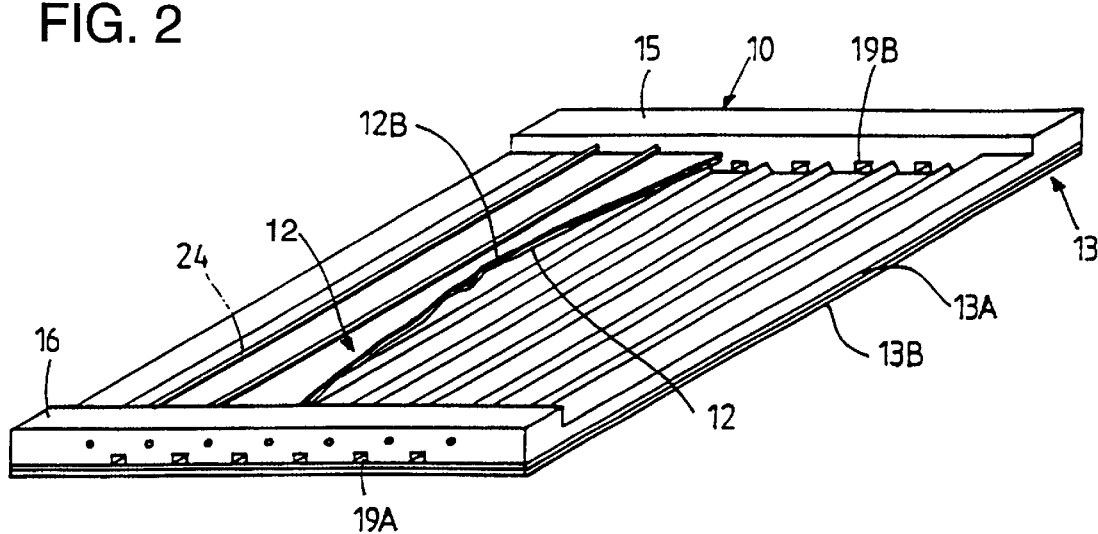
FIG. 2 is a view with cross-sections of a unit of the bioreactor of FIG. 1.

FIG. 2 shows a unit of the bioreactor of FIG. 1. Said unit comprises:
a) a frame 10;
b) gas permeable hollow fibers 24 extending between two opposite edges 15,16;
c) liquid permeable membranes 12A, 12B, 13A, 13B (with a porosity of 0.45 μm or 3 μm), between which a chamber similar to chamber 11 in FIG. 1 (see also FIG. 4) is formed for the flow of medium to be treated. In this unit, no collagen was used for fixing the cells.

Figure 3:
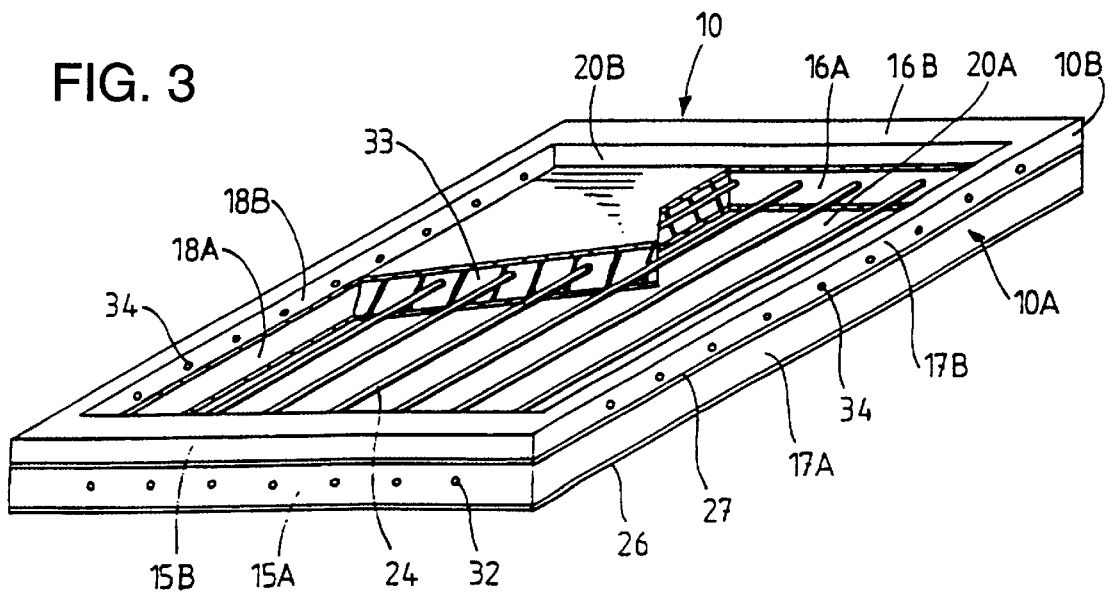
FIGS. 3 to 5 are views of other embodiments of units.

FIG. 3 shows another embodiment of a unit suitable for a bioreactor according to the invention.

Said unit comprises a frame 10 consisting of two elements 10A,10B having an outer rectangular pattern and having edges 15A,16A,17A,18A; 15B,16B,17B,18B defining a rectangular cavity 20A,20B.

An impermeable layer 36 forms the bottom of the cavity 20A, while a liquid permeable membrane 27 situated between the two elements 10A,10B forms the bottom of the cavity 20B and the top of the cavity 20A.

Between the edges 15A,16A extend hollow gas permeable hollow fibers 24 as well as plain fibers 32 acting as a means of reinforcement.

The edges 17B,18B have holes 34 so as to form passages for the inlet of medium to be treated in the cavity 20B and for the outlet of treated medium out of the cavity 20B.

The hollow fibers 24 are coated with a material, for example a material containing collagen, for making a surface an which the cells are attached. A material such as a hydrogel, PVA, HEMA, etc is used for filling the space between fibers in the cavity 20A. However it is advantageous to apply a thin layer of collagen or similar material above the said material for inducing cell adhesion, said thin layer forming the flat surface adapted to contact the liquid permeable membrane 27. In this case, the porosity of the membrane has for example pores with a diameter less than 0.5 μm.

The frame 10A,10B can be manufactured using potting compounds. For example, the hollow fibers are aligned longitudinally at a constant spacing.

Potting compound is then applied transversely at two places on the hollow fibers, places which are distant from each other by a distance corresponding to the length of the reactor.

Ends of the hollow fibers are so embedded into a matrix, the free ends of the hollow fibers being located at a face of the matrix so as to allow the passage of a gas through the hollow fibers.

The matrix in which the free ends of the hollow fibers are embedded may have a greater thickness than the rods linking said matrix. However in the embodiment shown in FIG. 3, the thickness of the frame 10 remains constant, but the material 33 filling the space with between fibers with the thin collagen layers on both sides fills only partly the volume defined by the frame, so that part of said volume is open or suitable for receiving a liquid medium to be treated.

Said unit is thus adapted to form with an adjacent unit a channel between the liquid permeable membrane of a first unit and the bottom layer of the adjacent unit, suitable for the flow of a liquid.

Figure 4:
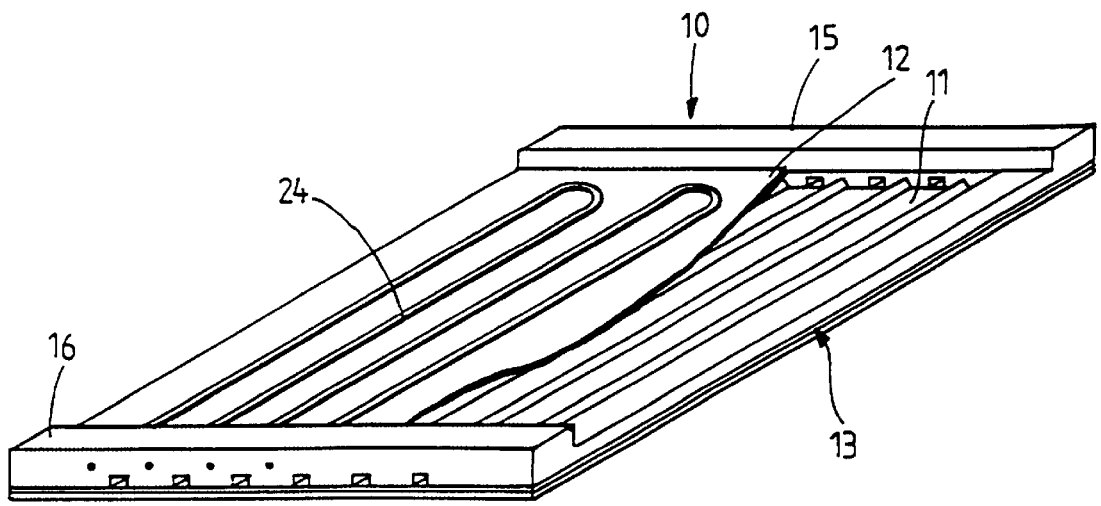

FIG. 4 shows a unit similar to that of FIG. 2, except that the (gas permeable hollow fibers) 24 have a (U-shape curved pattern), so that the inlet of gas in the fibers and the outlet of gas are located along one common edge 16 of the frame 10.

Figure 5:
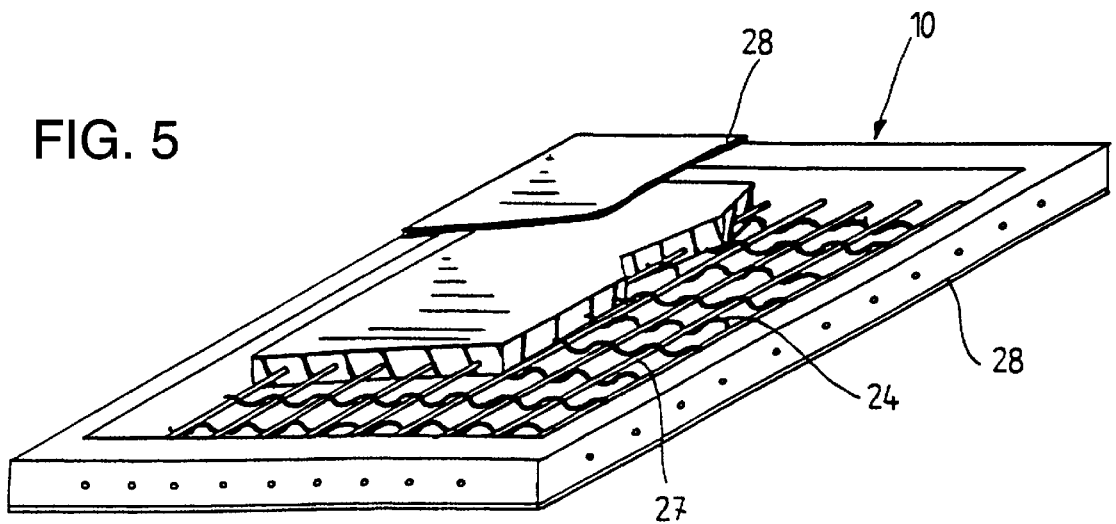

In the embodiment of FIG. 5, oxygenating means consist of hollow fibers 24 knitted with the hollow fibers 27 for the passage of the liquid to be treated. Said hollow fibers are for example embedded in the material such as hydrogel which fills the space between fibers. The frame 10 is advantageously provided on both side with an impermeable layer 28.

Figure 6:
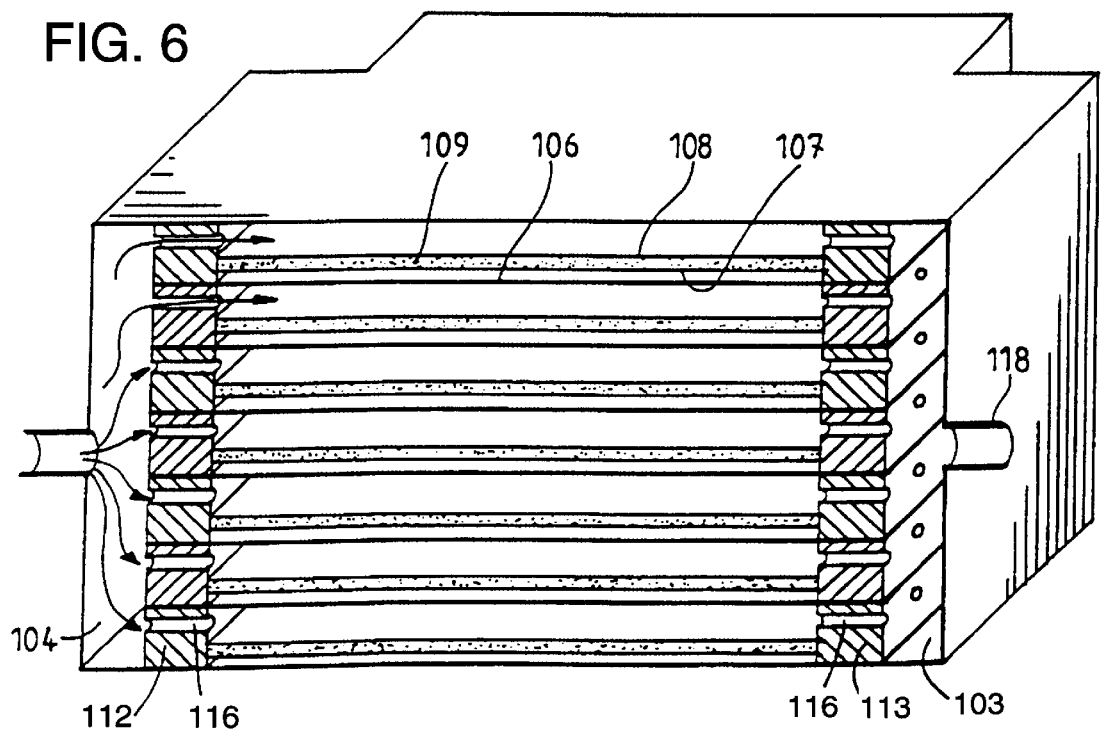
FIG. 6 is a partial perspective view with cross-sections of a bioreactor system according to the invention.
Figure 7:
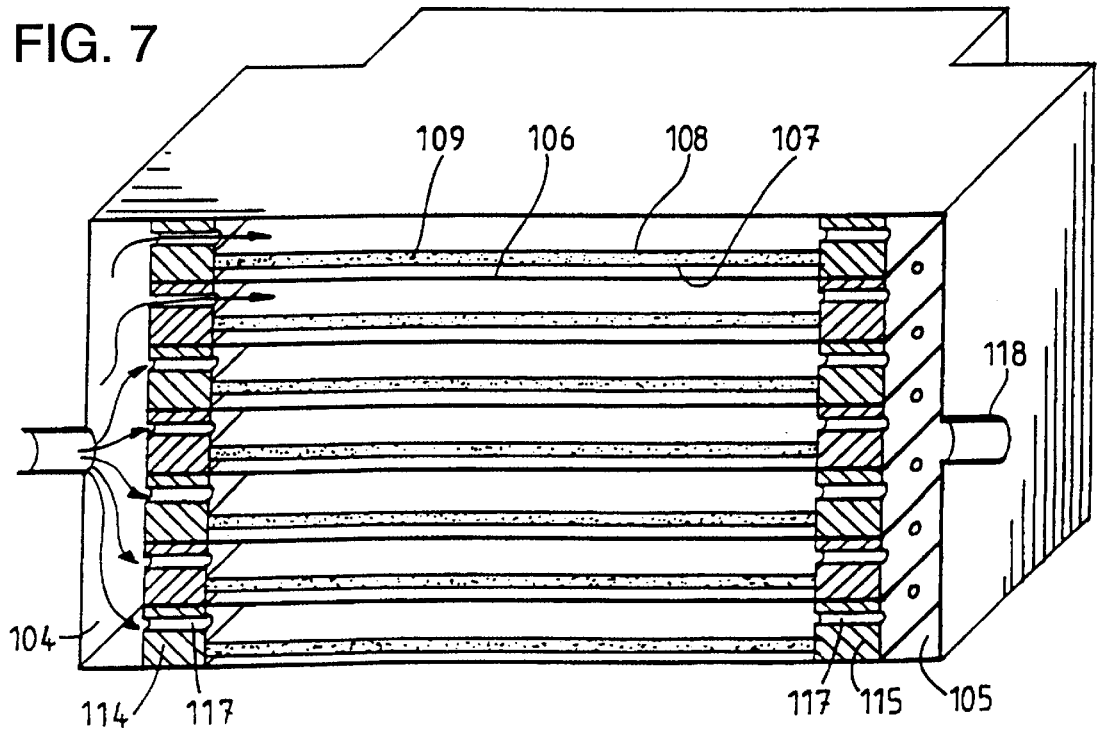
FIG. 7 is a cross-sectional view along the line VII—VII of FIG. 6.

FIGS. 6 and 7 are cross-sectional views of a bioreactor system 100 according to the invention.

Said bioreactor system 100 comprises a bioreactor 101, said bioreactor having an inlet collector or distributor 102 for the liquid flowing into the bioreactor, an outlet collector 103 for the liquid flowing out of the bioreactor, an inlet collector or distributor 104 for a gas, such as oxygen, flowing into the bioreactor and an outlet collector 105 for the gas flowing our of the bioreactor.

The bioreactor 101 comprises several units 1,2,3 consisting each of a frame 10 provided with a bottom impermeable layer 106, a liquid permeable membrane 107 and a gas permeable membrane 108.

Between the gas permeable membrane 108 and the liquid permeable membrane 107 is defined a chamber 109 for containing the cells (for example, a matrix containing cells).

Between the impermeable membrane 106 (intended to cover the frame 10 of an adjacent unit and to separate two adjacent units) and the liquid permeable membrane 107, a channel or passage 110 is formed for the liquid to be treated.

Between the gas permeable membrane 108 and a impermeable membrane or layer 106 of an adjacent unit or of the housing of the system, a passage or channel 111 is formed for the gas for oxygenating the cells.

The frame 10 has a rectangular shape and has four edges 112, 113, 114, 115. The opposite edges 112, 113 which are adjacent to one of the liquid collectors 102, 103 are provided with holes or passages 116 so that the liquid can flow from the inlet collector 102 into the channel(s) 110 of the unit of the bioreactor and can flow out of said channel(s) 110 into the outlet collector 103. The two other edges 114, 115 are also provided with holes 117 or engraved channels so as to allow the passage of gas into and out of the bioreactor 101.

Advantageously the outlet collector 103 for liquid is provided with a means ensuring the ultrafiltration of the liquid after treatment in the bioreactor, while on the outlet pipe 118 for evacuating or recycling gas issuing from the outlet gas collector 105, a means for reducing or increasing the flow of gas out of the bioreactor and thus in the bioreactor is incorporated. Such means are, for example a pump and valves for ensuring a specific pressure on the face of the gas permeable membrane, for example for ensuring that the pressure exerted on the gas permeable membrane is substantially equal or lower to the pressure exerted on the liquid permeable membrane. For example, gas is sucked out of the reactor. Such a sucking was found as being preferred for the regulation of the liquid flow.

The bioreactor of the invention has a well determined configuration allowing a high metabolic activity. Furthermore, such reactor is easy to produce and the number of units to be used can be adapted in order to take into consideration the patient requirement.

The bioreactor of the invention is suitable in many processes, such as a process for the treatment of cell cultures, in particular hepatocytes, on hollow fibers as porous films that are at least partly permeable to gas and/or liquid, so that the cell cultures are deposited on the film or hollow fibers, and the culture medium is led flowed through the hollow fibers or through a chamber.

In medicine and pharmacy, the bioreactor can be used for conducting tests with cell cultures, especially liver cells (hepatocytes). This applies, for instance, to their breeding, observation, especially observation of reactions with foreign matter and/or toxicants, conservation, etc.

Furthermore, the bioreactor is a solution to problems in the research for adequate organ replacements.

The bioreactor aims also at creating a process allowing for a mass culture, so as to obtain insofar as possible an "in vivo" condition, especially a lifetime as long as possible.

Preferably in the invention, the cell cultures are embedded in a extracellular matrix layer according to a sandwich technique known in itself. This ensures thus a reorganization of the cell pattern and a reformation of the microvillae on the side(s) facing the matrix surfaces. This matches the natural form of the liver cells and further the mass transfer in the way of sinusoidal membranes. Besides these morphological advantages, the maintenance of the function of these cells is also essential.

Figure 8:
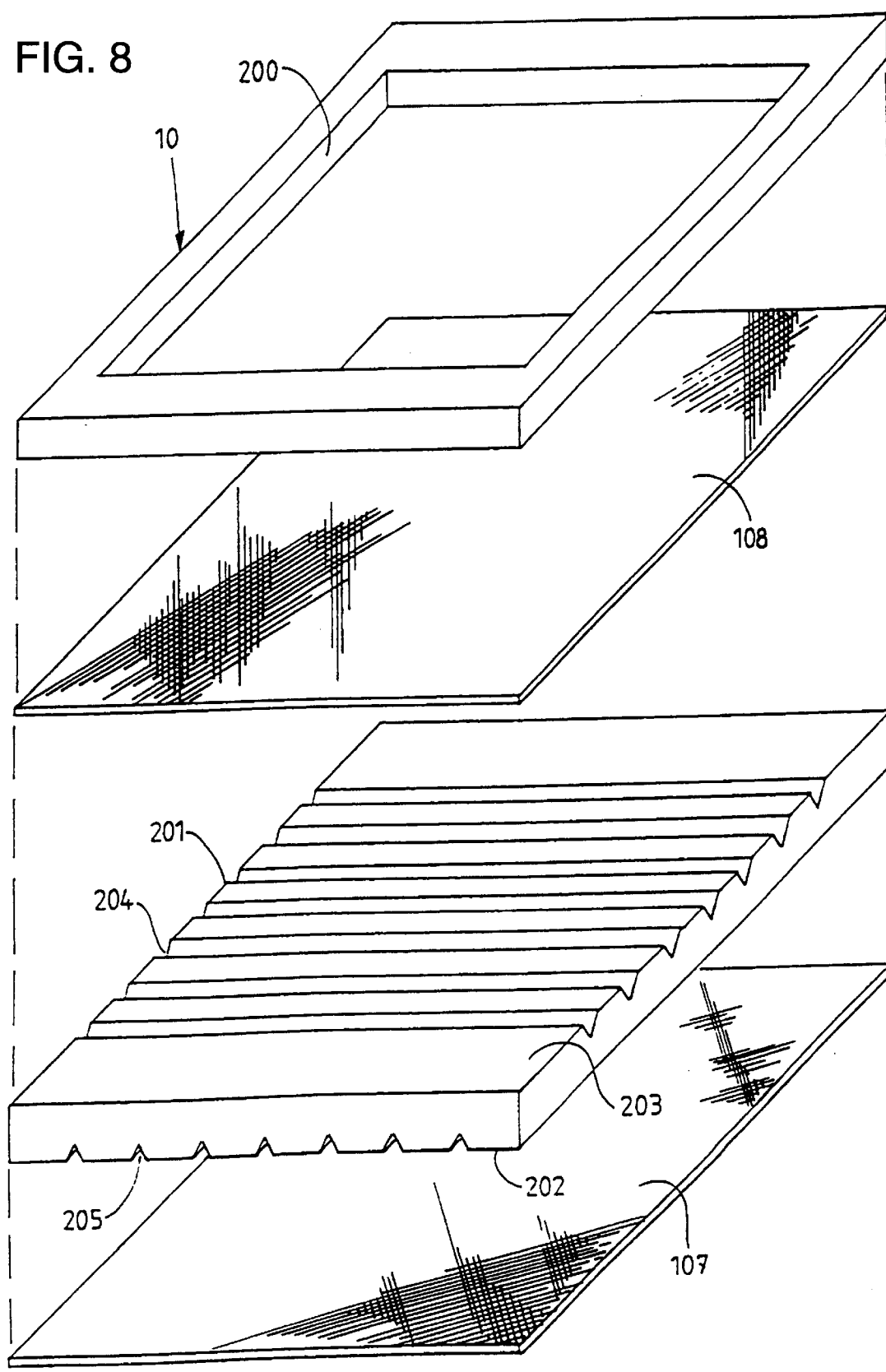
FIG. 8 is an exploded view of a further embodiment of a unit according to the invention.

FIG. 8 shows a further embodiment of a unit according to the invention. Said unit comprises a frame 10 with a central opening 200, a gas permeable membrane 108, a spacer 201 and a liquid permeable membrane 107. The spacer is provided on its opposite faces 202,203 with grooves 204, 205 so as to form channels for the passage of gas (204) and for the passage of liquid (205). In the embodiment shown, the channels are such that the flow of liquid is orthogonal to the flow of gas.

The gas permeable membrane 108 covers the bottom of the frame 10 and forms the bottom of a cavity intended to contain the cell or cells for the treatment.

According to a preferred embodiment, similar to that shown in FIG. 8, the spacer 201 is provided with the gas permeable membrane 108 and the liquid permeable membrane 107. The said plate and membranes form then a spacer intended to be located between two adjacent frames 200.

Figure 9:
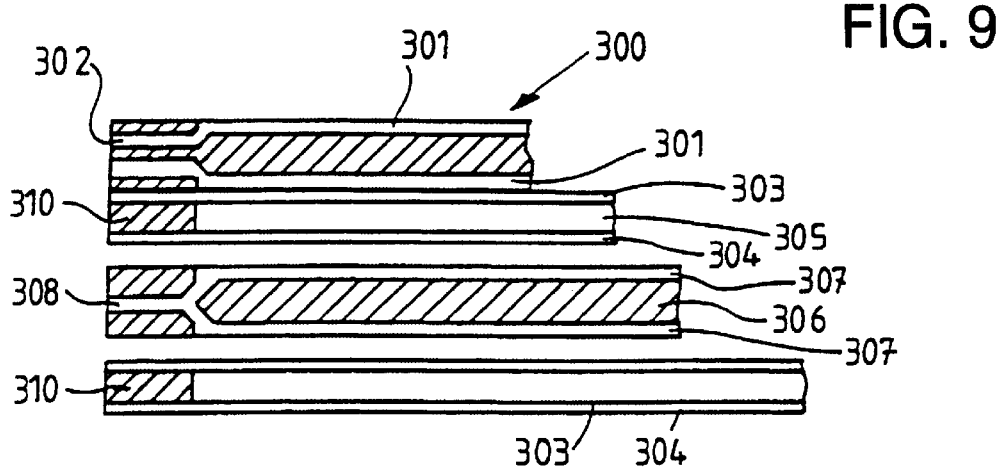
FIG. 9 is a cross-sectional view of still a further embodiment of a unit according to the invention.

FIG. 9 is a partial exploded cross-section view of another unit.

This unit comprises:

- a plate 300 provided on its opposite faces with grooves 301 intended to form channels for the passage of gas, and along at least one of its edges 302 with one or several holes so as to form a channel between said edge and the grooves 301;
- a frame 310 provided with a gas permeable membrane 303 and a liquid permeable membrane 304 so as to define between said membranes a chamber 305 for containing cells for the treatment.
- a plate 306 provided on its opposite faces with grooves 307, said grooves being linked to an inlet 308 and an outlet for the liquid to be treated or treated, and
- a frame 310 provided with a gas permeable membrane 303 and a liquid permeable membrane 304 so as to define between said membranes a chamber 305 for containing cells for the treatment.

Advantageously, the plate 300 is provided on its both faces with a gas permeable membrane 303, while the plate 308 is provided on its both faces with a liquid permeable membrane 304. The said plates 300, 308 with membranes form then a spacer to be located between two adjacent frames 310.

The fixing of the membrane on the plates is preferred for stacking purposes.

Figure 10:
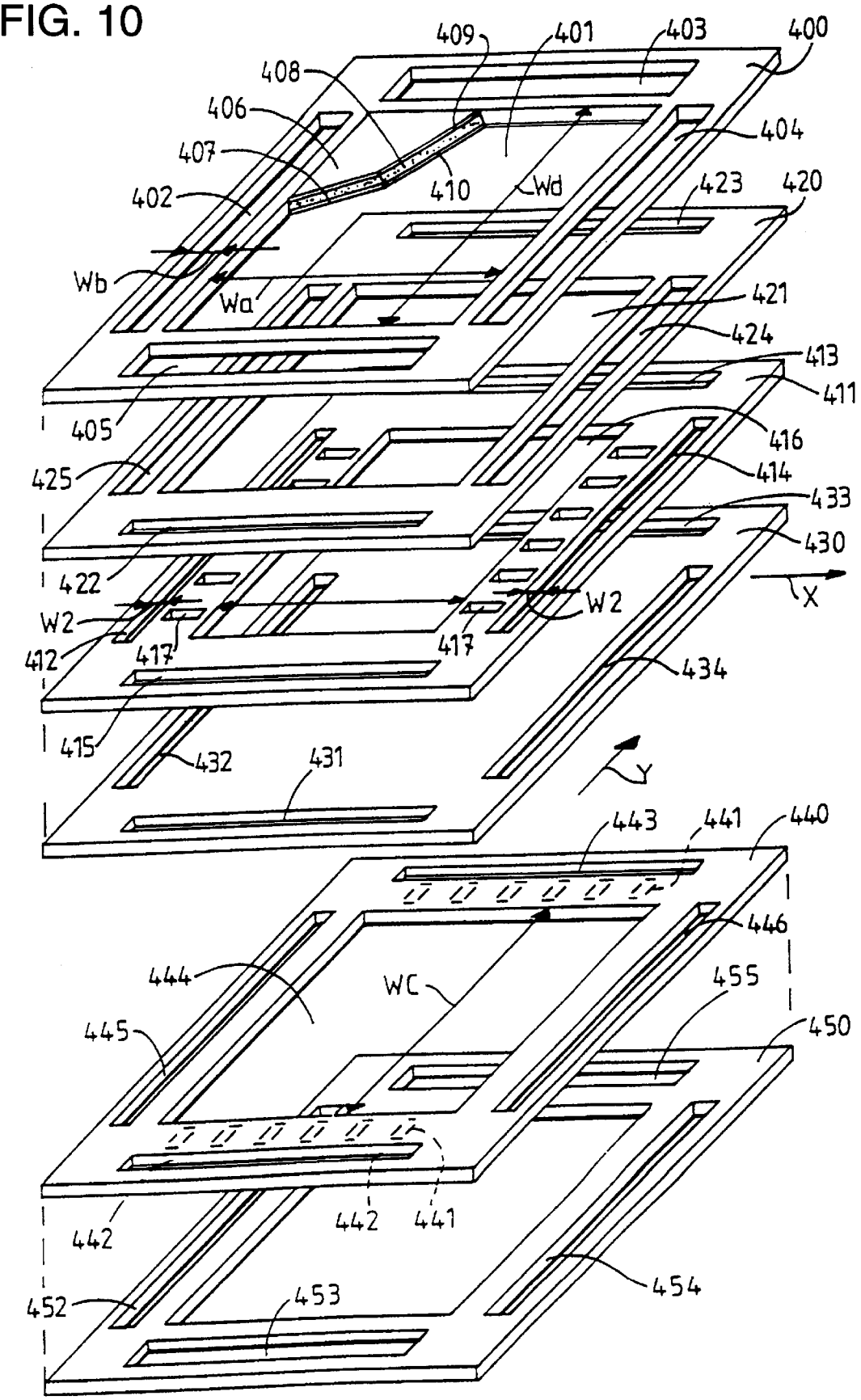
FIG. 10 is an exploded view of another embodiment of a unit according to the invention.

FIG. 10 is an exploded view of a unit according to the invention, units when stacked one on top of another form a bioreactor of the invention.

Said unit comprises:

- a square plate 400 with a central opening 401 and with lateral openings 402,403,404,405 along the edges of the plate 400, the central opening 401 being provided with a top gas permeable membrane 406, a bottom liquid permeable film 407 (consisting of two adjacent membranes), and, between said top gas permeable membrane and the bottom liquid permeable film, a layer of cells 408 entrapped with collagen layers 409, 410;

a square plate 420 with a square central opening 421 and with lateral openings 422,423,424,425;

a square plate 411 with four lateral openings 412,413, 414,415 and a central opening 416, whereby the central opening 416 and the lateral opening 412,414 have a width W1, W2 less than the width Wa,Wb of respectively the central opening 401 and the openings 402, 404 (width in the direction X); grooves 417 are located between the lateral openings 412,414 and the central opening 416;

a square plate 430 with only four lateral openings 431, 432,433,434;

a square plate 440 similar to the plate 411, except that the grooves 441 are located between the lateral openings 442,443 and that the width Wc of the central opening 444 (width in the direction Y perpendicular to the direction X) is less than the width Wd of the opening 401 (in the direction Y), and a square plate 450 similar to the plate 420.

Figure 11:
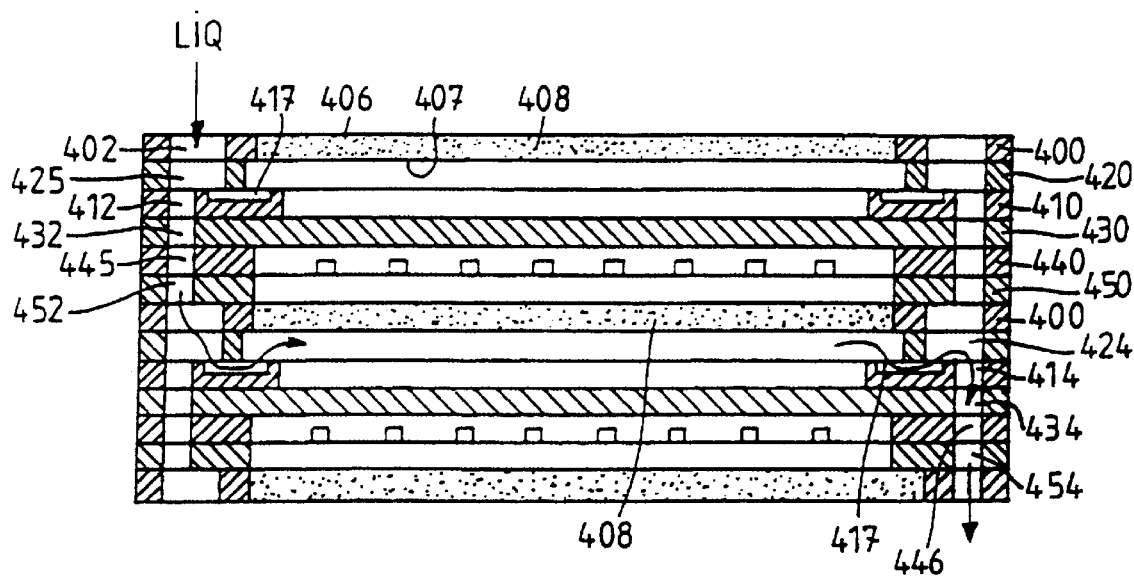
FIGS. 11 and 12 are cross-sectional views of the embodiment of FIG. 10, along the lines XI—XI and XII—XII.

The lateral openings 402,412,425,432,445 and 452 form a channel for the inlet flow of liquid to be treated while the lateral openings 404,414,424,434,446 and 454 form a channel for the outlet flow of the liquid after passage in front of the liquid permeable membrane 410 (i.e. through the grooves 417 and in the chamber formed by the openings 416 and 421) (see FIG. 11).

The lateral openings 403,413,423,433,443 and 455 form a channel for the outlet flow of a gas such as oxygen, while the lateral openings 405,415,422,431,442 and 453 form a channel for the inlet flow of gas.

Figure 12:
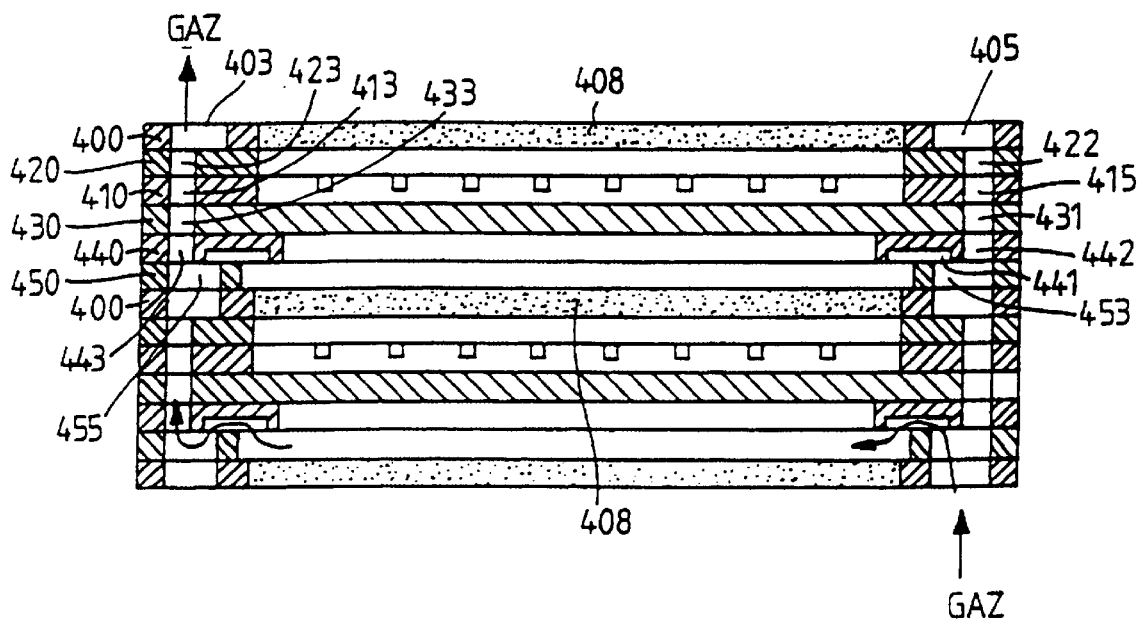

The gas flows in front of the gas permeable membrane 406, i.e. in and out of the cavity formed by the central openings 451 and 444 through the grooves 441 (see FIG. 12).

Figure 14:
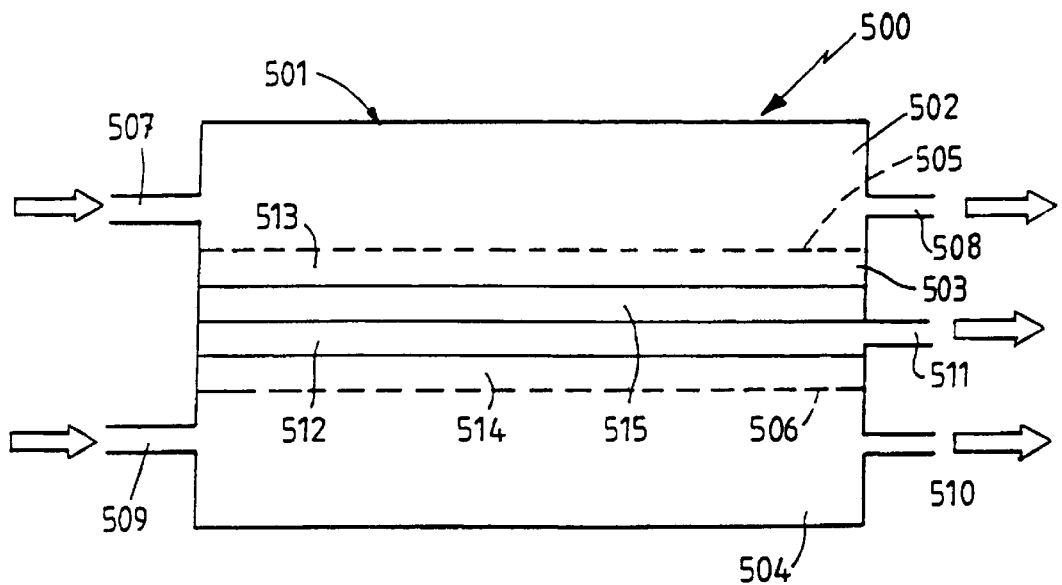
FIG. 14 is a view of a preferred bioreactor of the invention.

FIG. 14 shows a system 500 comprising a bioreactor 501. The bioreactor has a fluid compartment 502, a cell compartment 503 and a gas compartment 504, a liquid permeable membrane or a plurality of liquid permeable membranes 505, at least one of said membranes having pores with a diameter less than 0.45 $\mu$m, a gas permeable membrane 506, an inlet 507 for introducing the medium to be treated, and an outlet 508 for the medium flowing out of the fluid compartment 502, an inlet 509 and an outlet 510 for the gas compartment 504, and an outlet 511 for collecting fluid flowing out of the chamber or cell compartment 504.

The cell compartment 503 comprises two layers of cells 512,513. The cell compartment 503 comprises in the example shown a first collagen layer 514 adjacent to the gas permeable membrane 506, a layer of hepatocyte cells 512, a second layer of collagen 515 covering the layer 512, and a layer of Kupfer cells 513. Such a cell compartment is suitable for ensuring a co-culture.

As some biliary products can remain in the cells compartment 503, it is advisable to remove said products from the compartment in order to have a good and substantially constant function of the cells.

Figure 15:
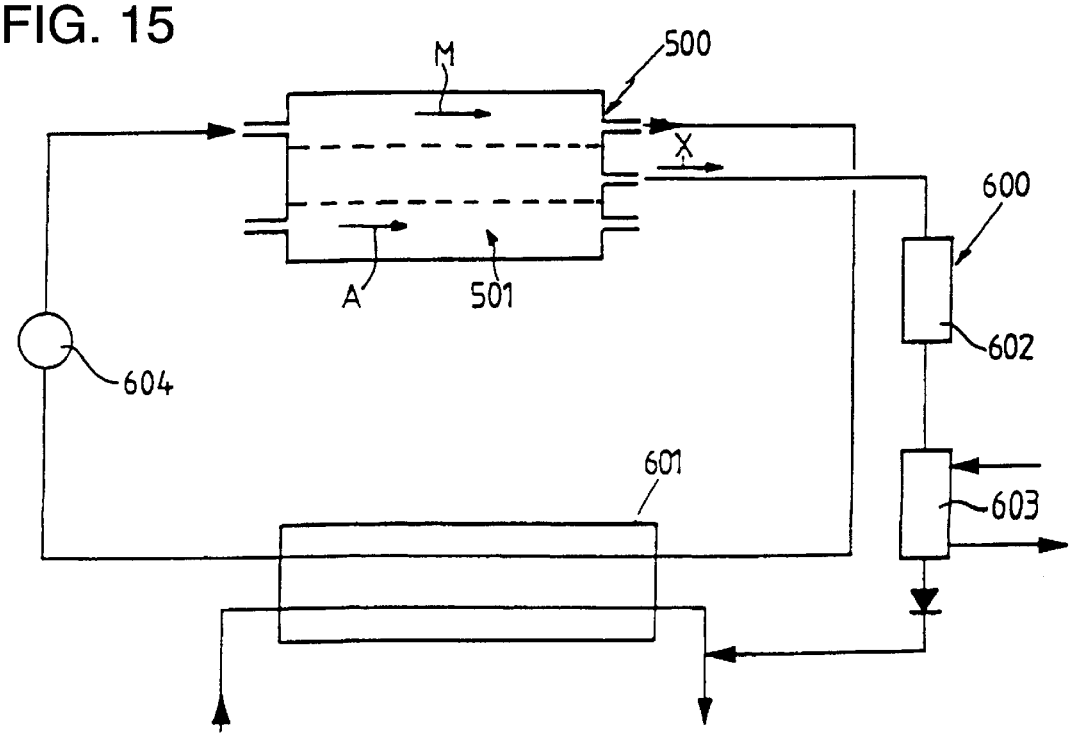
FIG. 15 is a schematic view of a system according to the invention.

FIG. 15 shows the system of FIG. 14 associated with a filtration means 600 and with an immunoisolation means 601. The filtration means comprises a filtrating membrane 602 avoiding the passage of particles with a diameter greater than 0.3 $\mu$m and a ultrafiltration means 603 so as to remove Creatinine, urea and other compounds.

The immunoisolation means is a means intended to isolate the blood flow of the patient from the bioreactor 501. Such an immunoisolation means comprises for example hollow fibres having hydrophobic and hydrophilic properties. For example, 50% of the fibres are hydrophobic or lipophilic fibers, while the other 50% of the fibers are hydrophilic.

A pump 604 ensures the flow of medium (M) through the bioreactor 501 and through the fibres of the immunoisolation means 601. Oxygen enriched air (A) flows through the bioreactor 501.

Medium (X) flowing out of the cell compartment is filtrated and ultrafiltrated, before being conveyed into the blood of the patient flowing out of the immunoisolation means.

The blood flow rate in the immunoisolation means is for example 600 ml/minute, while the plasma flow rate in the immunoisolation means and the bioreactor is 14 liters/minute.

The oxygenating medium can be for example a mixture of 20% $O_2$–80% $N_2$ for the phase for the attachment of cells, and a mixture of 10% $O_2$–90% $N_2$ for the phase of treatment.

The outflow of medium from the cell compartment and the recycling of said medium after filtration into the blood of the patient allow the transfer of modified hemoglobine (molecular weight of 4000–5000) into the blood.

Figure 13:
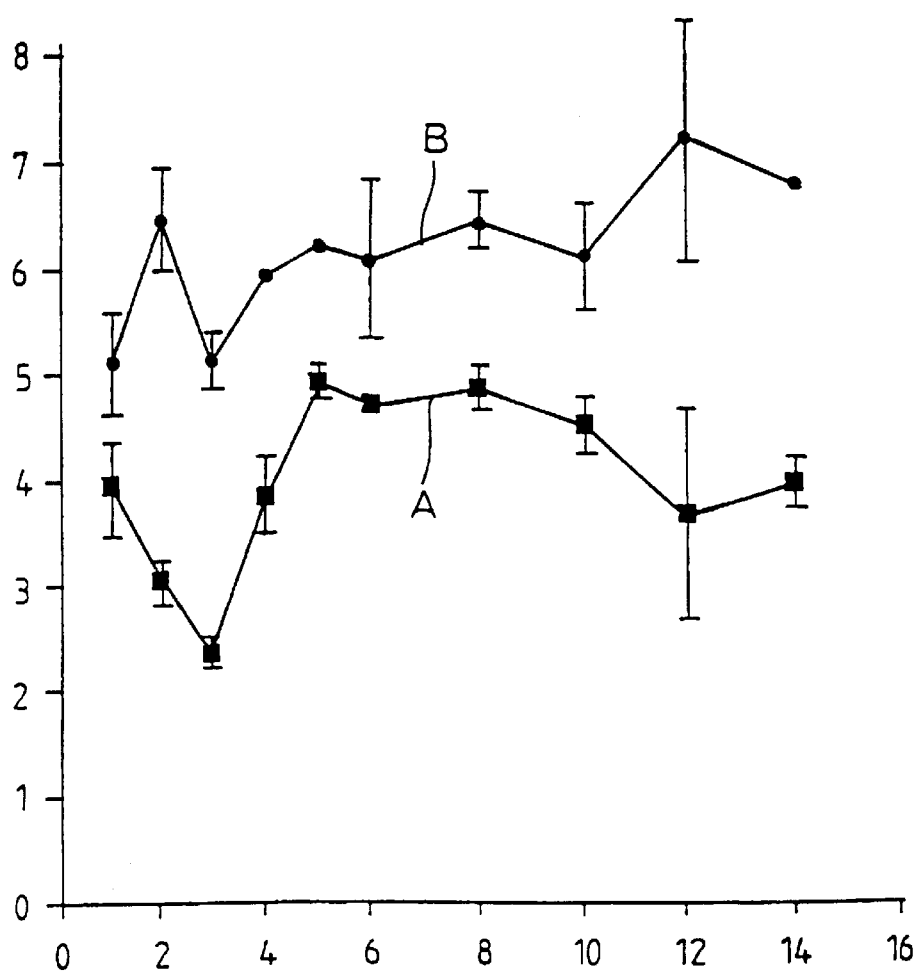
FIG. 13 is a graph showing the albumin secretion of primary hepatocytes cultured in presence of gas containing 10% (by volume) oxygen.

The efficiency of the bioreactor of the invention is depicted in FIG. 13.

Indeed, for primary hepatocytes placed on a plastic dish (curve A), the albumin secretion varies from about 2 to 5 $\mu$g/hour/$10^6$ cells (2 at day 3 and about 4 at day 14), while the albumin secretion (curve B) of primary hepatocytes in the bioreactor of the invention (a gas permeable membrane being used for the gas transfer) varies from about 5 to 7 (5 at day 3 and about 7 at day 14) $\mu$g/hour/$10^6$ cells.

Curve B is showing that the bioreactor design modus allows adequate oxygenation at physiologic oxygen tensions and indicates the increased efficiency of oxygen transfer with resulting higher synthetic function of the hepatocytes. These ambient oxygen tensions are lower than ordinarily used in standard cultures on impermeable supports (20% oxygen, cultures on collagen coated standard tissue culture plastic dishes).

By using the bioreactor of the invention, there is a much more constant secretion i.e. a more constant function of the bioreactor, the variation being less than 1 $\mu$g/hour/$10^6$ cells with respect to the mean value (about 6), i.e. a variation of about 15% or less.

When using plastic dishes without gas permeable membrane, the variation is about 1.5 $\mu$g/hour/$10^6$ cell with respect to the mean value (about 3.5), i.e. a maximum possible variation of about 40% with respect to the mean value.

It has to be pointed out that the bioreactor design of the invention allows a uniform distribution and delivery of oxygen to the cells during the attachment phase. Normally the culture medium circulation would need to be shut down to allow for the settlement of the cells. However during the attachment phase, cells have an increased demand for oxygen. In studies, an increased attachment efficiency was observed on gas permeable membranes. Shutting down the liquid circulation as in standard reactors is disadvantageous especially for primary cells.

The bioreactor of the invention is suitable for cells covered by collagen but also for cells not covered by collagen (e.g. hematopoetic cells, in fact most other cells besides hepatocytes do not need bipolar attachment to collagen).

Liquid permeable membranes are also gas-permeable. There may be conditions which do not necessitate a specific liquid circulation, especially with reference to cells, which are less shear force sensitive than hepatocytes. In this case, culture medium can flow also in the chamber containing the cells. In such a case an exclusively gas-permeable membrane could be located on both sides of the cell compartment for allowing cell attachment on both sides. The cell compartment needs then an inlet and an outlet so as to have a liquid circulation through the compartment.

The frame separating the gas permeable membrane and the liquid permeable membrane has advantageously an opening to fill in the cells.

The channels on the spacer or plate can be either engraved, impressed or applied using a mask.

What is claimed is:

1. Bioreactor for a cell treatment of a medium comprising:
   a first channel for the flow of medium;
   a second channel for the flow of an oxygen containing gas;
   a chamber containing at least two layers of cells for treating the medium wherein the layers are separated from one another by means of a collagen layer;
   a gas permeable membrane separating the chamber from the second channel;
   a film separating the chamber from the first channel, the film comprising two adjacent liquid permeable membranes, the first membrane having pores with diameters of about 3 µm, the second membrane having pores with diameters less than 3 µm.

2. Bioreactor according to claim 1, in which the adjacent liquid permeable membranes are selected from the group consisting of membranes with hydrophobic characteristics and membranes with a combination of hydrophobic and hydrophilic characteristics.

3. Bioreactor according to claim 1, in which the said chamber is provided with an outlet so as to remove medium issuing through the liquid permeable membrane from the channel in which flows the medium to be treated.

4. Bioreactor according to claim 1, in which a cells layer contains at least one cell or cells not present in the other cells layer.

5. Bioreactor according to claim 1, in which the chamber comprises an inlet and an outlet so that a flow of cell medium is possible.

6. Bioreactor according to claim 1, further comprising a frame around and supporting the membranes so as to define the first and second channels.

7. Bioreactor of claim 6, wherein the frame has a bottom layer which is not permeable and an upper layer which is liquid permeable, said layers covering the faces of the frame so as to define between said layers the channel for the flow of liquid medium.

8. Bioreactor of claim 1, further comprising an open topped frame defining the chamber.

9. Bioreactor of claim 8, wherein said sheet has on one of its faces at least one channel for the flow of liquid medium adjacent to a liquid permeable membrane and on its opposite face at least one channel for the flow of gas adjacent a gas permeable membrane.

10. The bioreactor of claim 1, in which the film comprises two adjacent liquid permeable membranes, a first membrane having pores greater than 3 µm, while the second membrane has pores with a diameter lower than 0.5 µm.

11. The bioreactor of claim 1, in which the membrane with pores with diameters greater than 3 µm is direct towards the chamber and the membrane with pores with diameters less than 3 µm is directed towards the first channel.

12. The bioreactor of claim 1, wherein the channels, chamber, and membranes are arranged to form a first modular unit, the bioreactor further comprising at least a second modular unit, substantially similar to the first modular unit, and stacked on the first modular unit so that the bottom of the second unit covers the top of the first unit.

13. The bioreactor of claim 1, further comprising a means for sucking gas out of the gas flow channel.

14. Bioreactor for a cell treatment of a medium comprising:
    a first channel for the flow of medium;
    a second channel for the flow of an oxygen containing gas;
    a chamber containing at least two layers of cells for treating the medium wherein the layers are separated from one another by means of a collagen layer;
    a gas permeable membrane separating the chamber from the second channel;
    a film separating the chamber from the first channel, the film comprising two adjacent liquid permeable membranes, the first membrane having pores with diameters of about 3 µm, the second membrane having pores with diameters less than 0.5 µm.

15. The bioreactor of claim 14, in which the membrane with pores with diameters of about 3 µm is direct towards the chamber and the membrane with pores with diameters less than 0.5 µm is directed towards the first channel.

16. A system for a cell treatment of a liquid medium comprising a bioreactor comprising:
    a first channel for the flow of liquid medium;
    a second channel for the flow of an oxygen containing gas;
    a chamber containing at least two layers of cells for treating the liquid medium wherein the layers are separated from one another by means of a collagen layer;
    a gas permeable membrane separating the chamber from the second channel;
    a film separating the chamber from the first channel, the film comprising two adjacent liquid permeable membranes, the first membrane having pores with diameters greater than 3 µm, the second membrane having pores with diameters less than 3 µm;
    an inlet for introducing the liquid medium to be treated into the first channel;
    an outlet for the liquid flowing out of the first channel;
    an inlet for the gas to flow in the second channel;
    an outlet for the gas flowing out of the second channel;
    an outlet for collecting liquid flowing out of the chamber; and
    a means of filtering the liquid flowing out of the chamber.

17. The system of claim 16, which comprises means for ultrafiltrating the liquid flowing out of the chamber.

18. The system of claim 17, in which the bioreactor is associated with an immunoisolation device, said device comprising permeable membranes for separating a flow of blood of a patient and the flow of medium to be treated in the bioreactor and flowing out from the bioreactor.

19. Liver support comprising a system for a cell treatment of a liquid medium comprising a bioreactor comprising:
    a first channel for the flow of liquid medium;
    a second channel for the flow of an oxygen containing gas;
    a chamber containing at least two layers of cells for treating the liquid medium wherein the layers are separated from one another by means of a collagen layer;
    a gas permeable membrane separating the chamber from the second channel;

a film separating the chamber from the first channel, the film comprising two adjacent liquid permeable membranes, the first membrane having pores with diameters greater than 3 µm, the second membrane having pores with diameters less than 3 µm;

an inlet for introducing the liquid medium to be treated into the first channel;

an outlet for the liquid flowing out of the first channel;

an inlet for the gas to flow in the second channel;

an outlet for the gas flowing out of the second channel;

an outlet for collecting liquid flowing out of the chamber; and a means of filtering the liquid flowing out of the chamber.

20. Process for cell differentiation, consisting of the use of a bioreactor for a cell treatment of a medium comprising:

a first channel for the flow of medium;

a second channel for the flow of an oxygen containing gas;

a chamber containing at least two layers of cells for treating the medium wherein the layers are separated from one another by means of a collagen layer, a gas permeable membrane separating the chamber from the second channel;

a film separating the chamber from the first channel, the film comprising two adjacent liquid permeable membranes, the first membrane having pores with diameters greater than 3 µm, the second membrane having pores with diameters less than 0.5 µm.

21. A bioreactor for a cell treatment of a liquid medium comprising:

a first chamber with cells for treating the medium;

a second chamber with cells for treating the medium, the second chamber spaced from the first chamber;

a liquid inlet for receiving the liquid medium;

a gas inlet for receiving an oxygen-containing gas;

a first plate between the first and second chambers and having:

a top surface with a first set of grooves defining a first set of channels fluidly coupled to the liquid inlet for providing flow of liquid medium, and a bottom surface with a second set of grooves defining a second set of channels fluidly coupled to the gas inlet for providing flow of the gas;

a first liquid permeable membrane separating the first chamber from the first set of channels; and a first gas permeable membrane separating the second chamber from the second set of channels.

22. The bioreactor of claim 21, wherein the first set of grooves are parallel to each other, the second set of groves are parallel to each other, and the first and second sets of grooves are perpendicular to each other.

23. The bioreactor of claim 21, further comprising a second plate having a surface with a third set of grooves defining a third set of channels fluidly coupled to the liquid inlet for providing flow of liquid medium, and a second liquid permeable membrane between the first chamber and the third set of channels in the first plate.

24. The bioreactor of claim 23, further comprising a third plate having a surface with a fourth set of grooves defining a fourth set of channels fluidly coupled to the gas inlet for providing flow of gas, and a second gas permeable membrane between the second chamber and the fourth set of channels in the third plate.

25. The bioreactor of claim 21, further comprising a second plate having a surface with a third set of grooves defining a third set of channels fluidly coupled to the gas inlet for providing flow of gas, and a second gas permeable membrane between the second chamber and the third set of channels in the second plate.

26. The bioreactor of claim 21, wherein the liquid permeable membrane includes two adjacent membranes with one having a mean pore size larger than the mean pore size of the other membrane.

27. The bioreactor of claim 26, wherein the mean pore size of one of the two membranes is greater than 3 microns, and the mean pore size of the other membrane is less than 3 microns.

28. The bioreactor of claim 21, wherein the first set of grooves distributes the liquid medium uniformly among the first set of channels.

29. The bioreactor of claim 21, wherein the second set of grooves distributes the oxygen-containing gas uniformly among the second set of channels.

30. A bioreactor for a cell treatment of a medium comprising:

a first channel for the flow of medium, a second channel for the flow of an oxygen containing gas, a chamber having cells for treating the medium, a gas permeable membrane separating the said chamber from the second channel in which the oxygen containing gas flows, and a film separating the said chamber from said first channel, said film comprising two adjacent liquid permeable membranes, a first membrane having pores with diameters greater than 3 µm, the second membrane having pores with diameter less than 3 µm.

31. A bioreactor for a cell treatment of a liquid medium comprising:

a first rectangular plate with a substantially impermeable central region;

a second rectangular plate under the first rectangular plate and having a central opening for carrying an oxygen-containing gas;

a third rectangular plate and having a central opening for carrying the liquid medium to be treated;

a fourth rectangular plate between the second and third rectangular plates and having a central opening filled with cells for performing treatment, and having a liquid permeable membrane separating the cells from the third rectangular plate, and a gas permeable membrane separating the cells from the second rectangular plate;

means for providing gas from a periphery on one side of the second rectangular plate to the periphery on an opposite side of the second rectangular plate; and means for providing liquid medium from a periphery on one side of the third rectangular plate to the periphery on an opposite side of the third rectangular plate.

32. The bioreactor of claim 31, further comprising a fifth rectangular plate having an impermeable central region, the fifth plate positioned so that the third plate is between the fourth plate and the fifth plate.

33. The bioreactor of claim 31, wherein the gas flows in a first direction and the liquid flows in a direction orthogonal to the first direction.

34. The bioreactor of claim 33, wherein the rectangular plates are arranged to form a first modular unit, the bioreactor further comprising at least a second modular unit, substantially similar to the first modular unit, and stacked on the first modular unit so that the bottom of the second unit covers the top of the first unit, the bioreactor further comprising a liquid distribution region for receiving the liquid medium and fluidly coupled to each of the units for providing medium thereto, and a separate gas distribution region for receiving gas and fluidly coupled to each of the units for providing the gas thereto.

* * * * *